United States Patent
Tilbrook et al.

(10) Patent No.: US 8,642,588 B2
(45) Date of Patent: Feb. 4, 2014

(54) SHORT-ACTING BENZODIAZEPINE SALTS AND THEIR POLYMORPHIC FORMS

(75) Inventors: Gary Stuart Tilbrook, Huntingdon (GB); Louisa Jane Cubitt, Cambridge (GB)

(73) Assignee: PAION UK Limited, Cambridge (GB)

( * ) Notice: Subject to any disclaimer, the term of this patent is extended or adjusted under 35 U.S.C. 154(b) by 779 days.

(21) Appl. No.: 12/373,457

(22) PCT Filed: Jul. 10, 2007

(86) PCT No.: PCT/GB2007/002583
§ 371 (c)(1),
(2), (4) Date: Nov. 13, 2009

(87) PCT Pub. No.: WO2008/007081
PCT Pub. Date: Jan. 17, 2008

(65) Prior Publication Data
US 2010/0075955 A1    Mar. 25, 2010

(30) Foreign Application Priority Data

Jul. 10, 2006  (GB) .................................. 0613693.1

(51) Int. Cl.
*A61P 25/20* (2006.01)
*A61K 31/55* (2006.01)
*C07D 401/04* (2006.01)

(52) U.S. Cl.
USPC .......................................... 514/220; 540/562

(58) Field of Classification Search
USPC .......................................... 514/220; 540/562
See application file for complete search history.

(56) References Cited

U.S. PATENT DOCUMENTS

| | | | |
|---|---|---|---|
| 3,933,794 A | 1/1976 | Hester, Jr. et al. | |
| 5,019,583 A | 5/1991 | Feldmann et al. | |
| 5,665,718 A | 9/1997 | Godel et al. | |
| 5,698,691 A | 12/1997 | Yukimas et al. | |
| 5,834,464 A | 11/1998 | Bock et al. | |
| 7,435,730 B2 * | 10/2008 | Feldman et al. | 514/220 |
| 7,485,635 B2 | 2/2009 | Feldman et al. | |
| 2010/0081647 A1 | 4/2010 | Tilbrook et al. | |

FOREIGN PATENT DOCUMENTS

| EP | 0166 356 | 1/1986 |
|---|---|---|
| WO | WO 96 20941 | 7/1996 |
| WO | WO 96 23790 | 8/1996 |
| WO | WO 00/69836 A | 11/2000 |
| WO | WO 2006/010620 | 2/2006 |

OTHER PUBLICATIONS

Diane O. Thompson: "Cyclodextrins-Enabling Excipients: Their Present and Future Use in Pharmaceuticals", in "Critical Reviews in Therapeutic Drug Carrier Systems", 1997, pp. 1-104.
Bauer et al., Prolonged sedation due to accumulation of conjugated metabolites of midazalam, Lancet 1995, p. 145-147.
Chambon et al., "Ethyl Loflazepate: A Prodrug from the . . . ", Drug Res 35 (II) Nr. 10, 1985, p. 1572-1577.
Dingemanse et al., "Pharmacokinetic-pharmacodynamic modeling of the EEG . . . ", British Journal of Anaesthesia, 1997, 567-574.
Feldmann et al., "Design, Synthesis, and Pharmacological Evaluation . . . ", J. Med. Chem., 1991, 34, 2202-2208.
Freyer et al., "Conformational Shifts at the BZR . . . ", Life Science, vol. 39, Pergamon Journals Ltd. 1986, pp. 1947-1957.
Hester et al.,"8-Chloro-1-methyl-6-phenyl-4H-s-..", J. Med. Chem. 1980, 23, 643-647.
Khan et al., "Synthesis of 3-Substituted 1,4-Benzodiazeptine-2-ones", Organic Preperations and Procedures Int. 10(3), 105-111, (1978).
Kilpatrick et al., "A Novel Ultra-Short-acting Benzodiazeptine", Anaesthesiology, 2007, pp. 60-66.
Ochs et al., "Comparative Single-Dose Kinetics of Oxazolam . . . ", J. Clin. Pharmacol, 1984, 24:446-451.
C.G Wermuth, Saishin Soyaku Kagaku Gekan, Technomics K.K., Sep. 25, 1999, pp. 347-365 and 452-453.
Teisuke Okano, Shin Yakuzaigaku Soron (revised 3rd Edit.), Nankodo Co., Ltd., Apr. 10, 1987, pp. 257-258, 26, 111, 256-25.

\* cited by examiner

*Primary Examiner* — Brenda Coleman
(74) *Attorney, Agent, or Firm* — Henry M. Feiereisen LLC; Ursula B. Day

(57) ABSTRACT

The invention relates to esylate salts of the compound of formula (I):

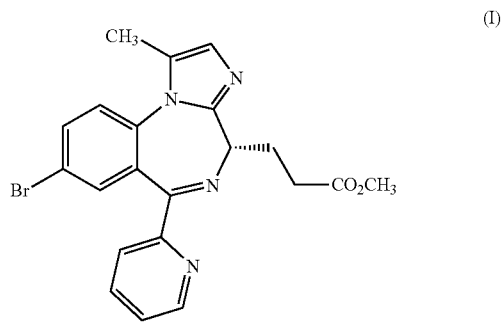

Methods of preparing the salts, and their use as medicaments, in particular for sedative or hypnotic, anxiolytic, muscle relaxant, or anticonvulsant purposes is also described.

21 Claims, 14 Drawing Sheets

Compound of Formula (I) Content (% Relative to Initial) vs Storage Temperature

A) Chromatograph of LJC-039-034-1 $T^0$

Figure 2 B) Chromatograph of LJC-039-034-1 $T^4$

XRPD comparing LJC-039-034-1 (esylate salt) pre and post 4 week stability study

XRPD overlay of new form of esylate

XRPD overlay of esylate generated in DCM and esylate slurried in DCM

Esylate Salt Form 1

A) XRPD: 100mg batch LJC-039-034-1

C) TGA: 100mg batch LJC-039-034-1

D) ¹H NMR: 100mg scale batch LJC-039-034-1

E) GVS: 100mg batch LJC-039-034-1

Figure 6 F) XRPD post GVS: 100mg batch LJC-039-034-1 esylate pre and post GVS

Figure 6 G) XRPD post stability study at 40°C/75%RH
LJC-039-034-1 pre and post 4 week stability study
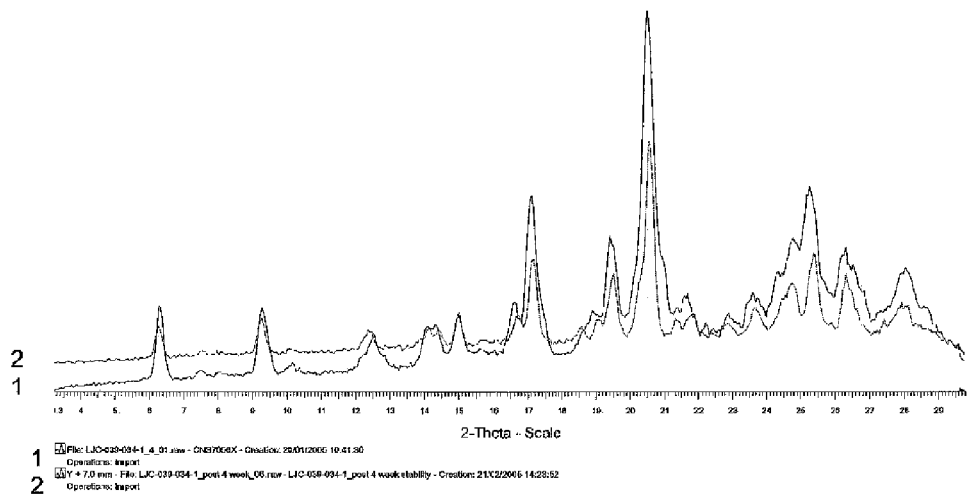
Figure 6 H) VT XRPD: 100mg batch LJC-039-034-1
VT LJC-039-034-1
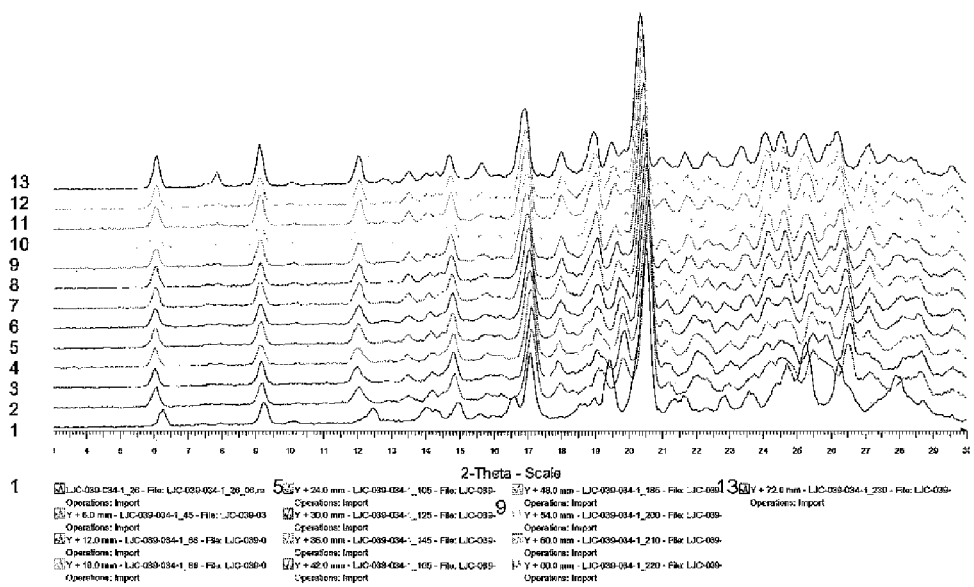
Temperature range from ambient to 230°C at 20°C increments.

l) Light Polarised Microscopy: 100mg batch LJC-039-034-1

Esylate Salt Form 2

A) XRPD: LJC-039-079-1

B) DSC: LJC-039-079-1

SHORT-ACTING BENZODIAZEPINE SALTS AND THEIR POLYMORPHIC FORMS

CROSS-REFERENCES TO RELATED APPLICATIONS

This application is the U.S. National Stage of International Application No. PCT/GB2007/002583, filed Jul. 10, 2007, which designated the United States and has been published as International Publication No. WO 2008/007081 and which claims the priority of Great Britain Patent Application, Serial No. GB0613693.1, filed Jul. 10, 2006, pursuant to 35 U.S.C. 119(a)-(d) the description of which is hereby incorporated by reference.

BACKGROUND OF THE INVENTION

This invention relates to salts of a short acting benzodiazepine, and to use of the salts as medicaments, in particular for sedative or hypnotic, anxiolytic, muscle relaxant, or anticonvulsant purposes.

European Patent No. 1,183,243 describes short-acting benzodiazepines that include a carboxylic acid ester moiety and are inactivated by non-specific tissue esterases. An organ-independent elimination mechanism is predicted to be characteristic of these benzodiazepines, providing a more predictable and reproducible pharmacodynamic profile. The compounds are suitable for therapeutic purposes, including sedative-hypnotic, anxiolytic, muscle relaxant and anticonvulsant purposes. The compounds are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anaesthetic or analgesic agents; ICU sedation.

One of the compounds disclosed in EP 1,183,243 (in Example Ic-8, page 36) is Methyl 3-[(4S)-8-bromo-1-methyl-6-(2-pyridinyl)-4H-imidazo[1,2-a][1,4]benzodiazepin-4-yl]propanoate, as shown in formula (I) below:

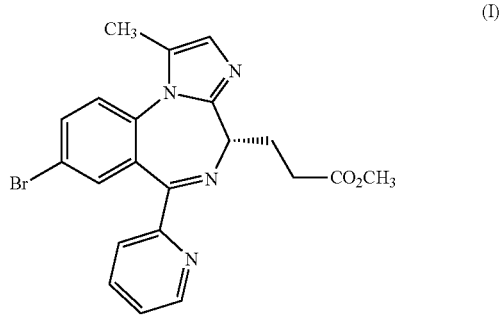 [SMILES: COC(=O)CC[C@@H]1N=C(c2ccccn2)c2cc(Br)ccc2-n2c(C)cnc21]

Whilst the free base of formula (I) is stable when stored at 5° C., samples stored at 40° C./75% relative humidity (open) are observed to deliquesce, become yellow to orange in colour, and show notable decreases in content relative to initial (see Example 1 below).

It has now surprisingly been found that the compound of formula (I) forms highly crystalline mono esylate (ethanesulphonic acid) salts that are easily isolated from a range of pharmaceutically acceptable solvents and show good thermal stability, low hygroscopicity and high aqueous solubility.

SUMMARY OF THE INVENTION

According to the invention there is provided an esylate salt of a compound of formula (I). Preferably the salt is a crystalline salt. Preparation and characterisation of polymorphic forms of esylate salts is described in the Examples below.

There is also provided according to the invention a crystalline polymorph of an esylate salt of a compound of formula (I) (herein designated esylate Form 1) that exhibits an X-ray powder diffraction (XRPD) pattern which comprises a characteristic peak at about 6.2, 9.2, 12.3, 15.0, 17.2, or 20.6 degrees two-theta.

Preferably the esylate Form 1 crystalline polymorph exhibits an XRPD pattern which comprises characteristic peaks at about 6.2, 9.2, 12.3, 15.0, 17.2, and 20.6 degrees two-theta.

More preferably the esylate Form 1 crystalline polymorph exhibits an XRPD pattern which comprises characteristic peaks at: 6.17 (19.30), 9.21 (20.50), 12.28 (16.40), 14.97 (23.40), 17.18 (52.80), 20.63 (100.00) [angle 2θ° (percentage relative intensity)].

Preferably the esylate Form 1 crystalline polymorph has a differential scanning calorimetry (DSC) onset melting temperature in the range 195-205° C., preferably about 201-202° C.

There is further provided according to the invention a crystalline polymorph of an esylate salt of a compound of formula (I) (herein designated esylate Form 2) that exhibits an X-ray powder diffraction (XRPD) pattern which comprises a characteristic peak at about 3.6, 6.4, 7.1, 12.3, 14.1, or 17.1 degrees two-theta.

Preferably the esylate Form 2 crystalline polymorph exhibits an XRPD pattern which comprises characteristic peaks at about 3.6, 6.4, 7.1, 12.3, 14.1, and 17.1 degrees two-theta.

More preferably the crystalline polymorph exhibits an XRPD pattern which comprises characteristic peaks at: 3.57 (15.60), 6.42 (21.10), 7.13 (58.30), 12.29 (51.50), 14.10 (58.90), 17.13 (68.00) [angle 2θ° (percentage relative intensity)].

Preferably the esylate Form 2 crystalline polymorph has a differential scanning calorimetry (DSC) onset melting temperature in the range 185-195° C., preferably about 190-191° C.

A preferred salt is the esylate Form 1 based on the robustness of formation, yield, purity and chemical and solid form stability.

There is also provided according to the invention a method of making an esylate salt of a compound of formula (I), which comprises reacting a free base of a compound of formula (I) with ethane sulphonic acid.

Also according to the invention there is provided a method of making a salt of the invention, which comprises contacting a free base of a compound of formula (I) with ethane sulphonic acid in solution to cause formation of a precipitate of the esylate salt, respectively. Preferably the method further comprises isolating the precipitate.

Preferably the free base is dissolved in toluene, ethanol, ethyl acetate, MtBE, dichloromethane (DCM), isopropyl acetate, ethyl formate, methanol, or acetone. More preferably the free base is dissolved in toluene or ethyl acetate. Preferably the ethane sulphonic acid is dissolved in ethanol.

The esylate Form 1 may be prepared by contacting a solution of a free base of a compound of formula (I) in toluene, ethanol, ethyl acetate, MtBE, DCM, acetone, isopropyl acetate, ethyl formate, or methanol with a solution of ethane sulphonic acid in ethanol to cause formation of a precipitate of the salt.

There is also provided according to the invention an esylate salt of a compound of formula (I) which is obtainable by the above method.

The esylate Form 2 may be prepared by slurrying the esylate Form 1 in DCM, or aqueous DCM (preferably 2.5% aqueous DCM) at a temperature above room temperature (preferably 60° C.) to form a solution, and evaporating the solution to dryness.

There is also provided according to the invention an esylate salt of a compound of formula (I) which is obtainable by the above method.

Salts of the invention may also be prepared by crystallising compound of formula (I) esylate from a suitable solvent, or from a suitable solvent/anti-solvent or solvent/co-solvent mixture. The solution or mixture may be cooled and/or evaporated to achieve crystallisation if appropriate.

The esylate Form 1 may be crystallised from ethanol, or from toluene/ethanol, ethyl acetate/ethanol, MtBE/ethanol, DCM/ethanol, acetone/ethanol, isopropyl acetate/ethanol, ethyl formate/ethanol, methanol/ethanol, or ethanol/water.

The esylate Form 2 may be crystallised from a solution of the esylate Form 1 in DCM or aqueous DCM (preferably the esylate Form 1 is dissolved in hot solvent, suitably about 60° C.).

There is also provided according to the invention an esylate salt of a compound of formula (I) obtainable by any of the above methods.

Methods of preparing salts of the invention are described in more detail in the Examples below.

A salt of the invention may be used as a medicament, in particular for sedative or hypnotic, anxiolytic, muscle relaxant, or anticonvulsant purposes.

While it is possible for a salt of the invention to be administered as a bulk active chemical, it is preferably provided with a pharmaceutically acceptable carrier, excipient, or diluent in the form a pharmaceutical composition. The carrier, excipient, or diluent must, of course, be acceptable in the sense of being compatible with the other ingredients of the composition and must not be deleterious to the recipient.

Accordingly, the present invention provides a pharmaceutical composition comprising a salt of the invention and a pharmaceutically acceptable carrier, excipient, or diluent.

Pharmaceutical compositions of the invention include those suitable for oral, rectal, topical, buccal (e.g. sub-lingual) and parenteral (e.g. subcutaneous, intramuscular, intradermal or intravenous) administration.

Preferably a salt of the invention is provided in the form of a pharmaceutical composition for parenteral administration, for example, by intravenous or intramuscular injection of a solution. Where the pharmaceutical composition is for parenteral administration, the composition may be an aqueous or non-aqueous solution or a mixture of liquids, which may include bacteriostatic agents, antioxidants, buffers or other pharmaceutically acceptable additives.

A preferred formulation of a salt of the invention is in an aqueous acidic medium of pH 2-4 or in an aqueous solution of a cyclodextrin (CD). Cyclodextrins that can be used for these formulations are either the anionically charged sulfobutylether (SBE) derivatives of β-CD, specifically SBE7-β-CD, marketed under the tradename Captisol by CyDex, Inc. (Critical Reviews in Therapeutic Drug Carrier Systems, 14 (1), 1-104 (1997)), or the hydroxypropyl CD's.

A further preferred formulation of a salt of the invention is a lyophilised formulation comprising, in addition to the salt, at least one of the following agents: ascorbic acid, citric acid, maleic acid, phosphoric acid, glycine, glycine hydrochloride, succinic acid or tartaric acid. These agents are believed to be useful as buffering, caking or visualisation agents. In some cases it may be beneficial to include sodium chloride, mannitol, polyvinylpyrrolidone, or other ingredients in the formulation.

The preferred method of formulation (i.e., acid buffer or CD-based) may depend on the physicochemical properties (e.g., aqueous solubility, pKa, etc.) of a particular salt. Alternatively the salt may be presented as a lyophilized solid for reconstitution with water (for injection) or a dextrose or saline solution. Such formulations are normally presented in unit dosage forms such as ampoules or disposable injection devices. They may also be presented in multi-dose forms such as a bottle from which the appropriate dose may be withdrawn. All such formulations should be sterile.

According to the invention there is provided a method for producing sedation or hypnosis in a subject, which comprises administering an effective sedative or hypnotic amount of a salt of the invention to the subject.

There is also provided according to the invention a method for inducing anxiolysis in a subject, which comprises administering an effective anxiolytic amount of a salt of the invention to the subject.

There is further provided according to the invention a method for inducing muscle relaxation in a subject, which comprises administering an effective muscle relaxant amount of a salt of the invention to the subject.

There is further provided according to the invention a method for treating convulsions in a subject, which comprises administering an effective anticonvulsant amount of a salt of the invention to the subject.

According to the invention there is also provided use of a sedative or hypnotic amount of a salt of the invention in the manufacture of a medicament for producing sedation or hypnosis in a subject.

According to the invention there is also provided a salt of the invention for producing sedation or hypnosis in a subject.

There is also provided according to the invention use of an anxiolytic amount of a salt of the invention in the manufacture of a medicament for producing anxiolysis in a subject.

There is also provided according to the invention a salt of the invention for producing anxiolysis in a subject.

There is further provided according to the invention use of a muscle relaxant amount of a salt of the invention in the manufacture of a medicament for producing muscle relaxation in a subject.

There is further provided according to the invention a salt of the invention for producing muscle relaxation in a subject.

There is further provided according to the invention use of an anticonvulsant amount of a salt of the invention in the manufacture of a medicament for treating convulsions in a subject.

There is further provided according to the invention a salt of the invention for treating convulsions in a subject.

The subject is suitably a mammal, preferably a human.

A suitable pharmaceutical parenteral preparation for administration to humans will preferably contain 0.1 to 20 mg/ml of a salt of the invention in solution or multiples thereof for multi-dose vials.

Intravenous administration can take the form of bolus injection or, more appropriately, continuous infusion. The dosage for each subject may vary, however, a suitable intravenous amount or dosage of a salt of the invention to obtain sedation or hypnosis in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to obtain anxiolysis in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to obtain muscle relaxation in a mammal would be 0.01 to 5.0 mg/kg of body weight, and more particularly, 0.02 to 0.5 mg/kg of body weight, the above being based on the weight of the salt which is the active ingredient. A suitable intravenous amount or dosage of a salt of the invention to treat convulsions in a mammal would be 0.01 to 5.0 mg/kg of body weight, and more particularly, 0.02 to 0.5 mg/kg of body weight, the above being based on the weight of the salt which is the active ingredient.

Salts of the invention are short-acting CNS depressants that are useful to be administered intravenously in the following clinical settings: preoperative sedation, anxiolysis, and amnestic use for perioperative events; conscious sedation during short diagnostic, operative or endoscopic procedures; as a component for the induction and maintenance of general anesthesia, prior and/or concomitant to the administration of other anaesthetic or analgesic agents; ICU sedation.

BRIEF DESCRIPTION OF THE DRAWINGS

Preferred embodiments of the invention are described in the following Examples with reference to the accompanying drawings in which.

DETAILED DESCRIPTION OF PREFERRED EMBODIMENTS

Example 1

Solid-State Stability Study of Compound of Formula (I)

Method/Technique. 2 mg samples of compound of formula (I), accurately weighed, were placed in 4-mL clear glass screw-cap vials. Samples were tested at initial and after 34 days stored at 5° C./Ambient Relative Humidity (AMRH) Closed, 30° C./60% RH Closed, 40° C./75% RH Open and 60° C./AMRH Closed.

Samples were inspected visually for appearance. Compound of formula (I) content values were determined by the HPLC method in Table 1. The % weight/weight (% w/w) values were measured relative to standard samples of compound of formula (I) Batch U12438/79/1. The % area values were obtained by dividing the compound of formula (I) peak area by the total peak area.

TABLE 1

HPLC Method Condition

| Column: | |
|---|---|
| Phase = | Phenomenex Luna C18(2) |
| Length × i.d = | 100 × 4.6 mm |
| Particle size = | 3 μm |
| Mobile phase: | A = 1000:1 Water/Trifluoroacetic Acid |
| | B = 1000:0.5 Acetonitrile/Trifluoroacetic Acid |
| Flow rate: | 1.0 mL/min |
| Column Temperature: | 40° C. |

| Gradient | Time (min) | % A | % B |
|---|---|---|---|
| | 0.0 | 80 | 20 |
| | 20.0 | 20 | 60 |
| | 25.0 | 20 | 60 |
| | 25.1 | 80 | 20 |
| | 30.0 | 80 | 20 |

| Detection Wavelength: | 230 mm |
|---|---|
| Sample Mass Injected | μg, typically 1 μL injection of 1.0 mg compound of formula (I)/mL in 60:40 Water/Acetonitrile |
| Retention Times | Compound of formula (I) elutes at approximately 7.64 min |

Results

Appearance. Table 2 lists the appearance results.

TABLE 2

Summary of Compound of Formula (I) Appearance Data

| Storage Condition | Timepoint days | Appearance |
|---|---|---|
| RT | initial | Cream to light yellow powder |
| 5 C./AMRH Closed | 34 | Cream to light yellow powder |
| 30 C./60% RH Closed | 34 | Cream to light yellow powder |
| 40 C./75% RH Open | 34 | Deliquesced yellow mass on bottom of vial |
| 60 C./AMRH Closed | 34 | Deliquesced dark yellow to orange mass on bottom of vial |

Compound of Formula (I) Content (% w/w). The % w/w content values (see Table 3) show too much variability to detect differences between the initial value and those measured after 34 days at 5° C./AMRH Closed, 30° C./60% RH Closed or 40° C./75% RH Open. The average % w/w measured for the samples stored 34 days at 60° C./AMRH Closed show a 10% w/w decrease from the initial value.

Figure 1:
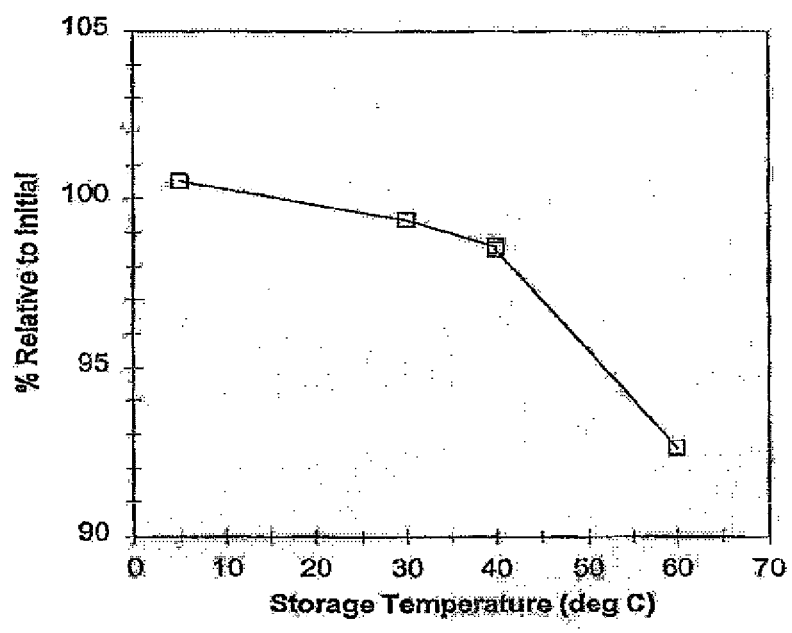
FIG. 1 shows a graph of compound of formula (I) content (% relative to initial) vs storage temperature.

Compound of Formula (I) Content (% area). The compound of formula (I) % area content (see Table 3 and FIG. 1) shows no significant change after 34 days stored at 5° C./AMRH Closed, but decreases steadily with increasing storage temperature for samples at 30° C./60°/GRH Closed, 40° C./75% RH Open or 60° C./AMRH Closed. Major degradation peaks are observed at RRT 0.68, 0.87 and RRT 0.90, but the chromatograms, which are relatively complex even at initial (23 peaks), also show many new small degradent peaks (e.g 7 peaks at 30° C./60% RH Closed; 13-20 peaks at 60° C./AMRH Closed). These observations suggest multiple degradation pathways. The degradant at RRT 0.68 is tentatively identified as the ester hydrolysis product (the free acid of compound of formula (I)). It is most prevalent in the 40° C./75% RH Open samples, as would be expected for a hydrolysis product.

TABLE 3

Summary of Compound of Formula (I) HPLC Data

| Storage Condition | Timepoint Days | Compound of formula (I) Content % w/w | % area | % Relative to Avg. Initial % area |
|---|---|---|---|---|
| RT | initial | 100.5 | 95.14 | Avg = 94.81 |
| RT | initial | 104.1 | 94.47 | |
| 5 C./AMRH Closed#1[1] | 34 | 102.6 | 95.30 | 100.52 |
| 30 C./60% RH Closed #1[1] | 34 | 94.7 | 94.20 | 99.36 |
| 40 C./75% RH Open #1 | 34 | 105.4 | 93.45 | 98.57 |
| 40 C./75% RH Open #2 | 34 | 100.3 | 93.39 | 98.50 |
| 60 C./AMRH Closed #1 | 34 | 93.4 | 87.77 | 92.57 |
| 60 C./AMRH Closed #2 | 34 | 91.1 | 87.77 | 92.57 |

Notes
[1] Only one sample was tested due to an autosampler sequencer error.

CONCLUSIONS

Compound of formula (I) is stable with respect to appearance and content for at least 34 days stored at 5° C./AMRH Closed. No change in appearance was noted at 30° C./60% RH Closed, but an approximately 0.6% drop in compound of formula (I) content relative to the initial % area was observed. Samples stored at 40° C./75% RH Open or 60° C./AMRH Closed deliquesced, became yellow to orange in colour and showed notable decreases (1.5 to 8%) in compound of formula (I) content relative to initial. Major degradation peaks at RRT 0.68, 0.87 and RRT 0.90 are observed along with numerous smaller peaks, suggesting multiple degradation pathways. The degradant at RRT 0.68 is tentatively identified as the ester hydrolysis product. These results indicate that compound of formula (I) should be stored refrigerated for long term storage.

Example 2

The solubility of the compound of formula (I) was determined in a wide range of organic solvents. The solubility data is shown in Table 4 below.

TABLE 4

| Solvent | Min solvent required/ mg/ml |
|---|---|
| Methanol | 446 |
| Ethanol | 324 |
| Propan-2-ol | 454 |
| Acetone | 214 |
| Toluene | 460 |
| Ethyl acetate | 218 |
| Tetrahydrofuran | 311 |
| Acetonitrile | 362 |

The data clearly shows that the compound of formula (I) has high solubility in common organic solvents. The preferred solvents are ethanol and toluene.

Two basic centres of the free base of the compound were measured for pKa. However, the basic centre of the pyridine ring had a pKa of 1.99. The pKa of the basic centre of the imidazole ring was measured to be 4.53.

Ethane sulphonic acid was used to produce esylate salts of the compound of formula (I). Experiments were conducted on a 20 mg scale using 6 volumes of solvent. All reactions were carried out at ambient temperature with acids charged as stock solutions in ethanol (1M) or as solids depending on solubility.

All solids isolated showed significant peak shifts in $^1$H NMR to confirm salt formation. X-Ray Powder Diffraction (XRPD) showed that all of the salts had crystalline indication. Table 5 summarises the isolated salt forms.

TABLE 5

| Entry | Salt | Solvent | ID |
|---|---|---|---|
| 1 | esylate | toluene | LJC-039-009-6 |
| 2 | esylate | EtOH | LJC-039-009-8 |

The salts were subsequently stored at 40° C./75% RH for two weeks then re-analysed by XRPD and HPLC for chemical purity to assess stability of the materials. The salts retained the same powder pattern after exposure to the humidity conditions, and also retained high chemical purity supporting improved stability.

It can be seen from the $T^1$ purity results of the isolated salts (Table 6 below) that in particular the esylate salt from toluene showed high purity values before and after the stability study.

TABLE 6

Summary of purity before and after 40° C./75% RH for 1 week

| Entry | Salt | ID | Purity $T^0$/% | Purity $T^1$/% |
|---|---|---|---|---|
| 1 | esylate | LJC-039-009-6 | 96.7 | 96.4 |
| 2 | esylate | LJC-039-009-8 | 92.8 | 89.4 |

The results above show that the esylate salt forms showed high purity and favourable stability results.

Example 3

Scale up of the esylate salts to 100 mg was performed based on data in Example 2. Toluene was found to be the preferred solvent for isolating esylate salts.

Esylate Salt of Compound of Formula (I)

A scale up to 50 mg of input material was carried out in order to confirm whether or not the process would scale up, and to confirm that the material isolated was of the same crystalline form (Form 1) seen from the smaller scale experiments. Once the analysis confirmed the salt to be Form 1 and that the properties were in keeping with what was expected, another scale up was carried out with 100 mg of input material in order to be able to carry out full characterisation and submit the sample for a 4 week stability study at 40° C./75% RH. Both the scaled up reactions were carried out in toluene with ethane sulphonic acid added as a solution in ethanol (1M). At this stage toluene had given the best results in terms of producing highly crystalline material in relatively high yield, and so was the solvent of choice.

Esylate Experimental Procedure

Compound of formula (I) free base (100 mg, batch 704-17) was charged to a vial and ethyl acetate (600 µl) was added at ambient. To the solution ethane sulphonic acid (250 µl, 1M in ethanol) was added and the reaction mixture and stirred overnight. After stirring overnight a solid had precipitated out of solution which was filtered, washed with ethyl acetate and oven dried at 40° C. under vacuum. Analysis by XRPD showed the solid to be of identical powder pattern as other esylates generated, and the $^1$H NMR confirmed salt formation due to significant peak shifts and peaks corresponding to ethane sulphonic acid counter ion.

The esylate salt showed the same powder pattern when isolated from 5 different solvents; toluene, ethanol, ethyl acetate, MtBE and DCM. The salt isolated from ethyl acetate was chosen as the salt on which to carry out full characterisation (Table 7).

TABLE 7

| Entry | ID | salt | GVS uptake/% | Onset melt/°C. | TGA weight loss/% | Solubility mg/ml | Chemical purity/% | Chiral purity/% e.e |
|---|---|---|---|---|---|---|---|---|
| 1 | LJC-039-034-1 | Esylate | 2.0 | 201.9 | 6.2 | 7.8 | 97.2 | 96.3 |

Process Optimisation

To improve further yields of esylate salts (Form 1) four solvents were screened (isopropyl acetate, ethyl formate, methanol and acetone). In total eight 100 mg scale reactions were conducted in these solvents with the relevant acid added as stock solution in ethanol for comparison to all previous experiments.

Compound of formula (I) (batch 704-38, 100 mg) dissolved in solvent (600 µl) at ambient. Acid (250 µl, 1M stock solution in ethanol) added and all reaction mixtures stood for 48 hours at ambient. The results are summarised in Table 8.

TABLE 8

Results of process optimisation experiments

| Table entry | Lab book reference | Salt | Solvent | XRPD | Yield/% | Purity/% area | Purity post 40° C./75% RH for 4 weeks |
|---|---|---|---|---|---|---|---|
| 1 | LJC-039-067-1 | esylate | acetone | Form 1 | 50 | 98.8 | 98.4 |
| 2 | LJC-039-067-3 | esylate | iPrOAc | Form 1 | 61 | 98.5 | 98.6 |
| 3 | LJC-039-067-5 | esylate | Ethyl formate | Form 1 | 53 | 99.0 | 98.9 |
| 4 | LJC-039-067-7 | esylate | MeOH | Form 1 | 100 (evaporated to dryness) | 97.1 | Not recorded |

All reactions showed Form 1.

It was concluded from the study that solvents such as isopropyl acetate increased the purity of the salts, however reduced the recovery. Because the previous choice of solvent (ethyl acetate) gave high yielding salts with high purity values, it was decided to use ethyl acetate for the final scale up experiments.

Esylate Aqueous Solvents Studies

In Example 2 it was observed that forming the esylate salt from ethanol not only reduced the purity, but also lead to an impurity thought to be the acid as a result of the ester hydrolysis. In order to determine if this was the case, a study was carried out using ethanol as solvent, with varying amounts of water. The general procedure was as follows:

Compound of formula (I) (4×20 mg) dissolved in ethanol (4×120 µl, neat, 2, 5 or 10% $H_2O$). Ethane sulphonic acid (50 µl, 1M in ethanol) was added to the solutions. The reaction mixtures were stood at ambient for 16 hours after which time all remained as solutions. The solutions were concentrated by evaporation for 16 hours. The vials containing 5 and 10% $H_2O$ required anti-solvent treatment to encourage precipitation, whereas the neat ethanol reaction mixture had oiled and was therefore triturated with diethyl ether. The reaction mixture containing 2% $H_2O$ contained solid that appeared to have crystallised from an oil. All four solids were crystalline by XRPD analysis and they all showed the same powder pattern as previous esylate salts isolated. The samples were submitted for chemical purity.

TABLE 9

Purity data of aqueous solvent study

| Entry | ID | % $H_2O$ | Purity/% |
|---|---|---|---|
| 1 | LJC-039-047-1 | 0 | 93.9 |
| 2 | LJC-039-047-2 | 2 | 90.9 |
| 3 | LJC-039-047-3 | 5 | 94.7 |
| 4 | LJC-039-047-4 | 10 | 90.0 |

The study showed no significant change in purity of samples derived from neat or aqueous ethanol mixtures. It was also noted that there were negligible amounts of acid impurity present by HPLC, implying the small amount of water in the system was not sufficient to catalyse the hydrolysis.

The next stage was to determine the stability of all the salts by subjecting them to conditions of 40° C./75% RH for 4 weeks and monitoring their purity by HPLC (Table 10).

Example 4

Salt Stability Studies

TABLE 10

Summary Table of salt purities after 4 week stability study

| Sample ID | salt | $T^0$ | $T^1$ | $T^2$ | $T^3$ | $T^4$ |
|---|---|---|---|---|---|---|
| LCJ-039-034-1 | Esylate | 97.2 | 97.1 | 97.0 | 97.2 | 97.0 |

Crystalline samples of esylate were stored at 40° C./75% RH for a total of four weeks and samples were taken for HPLC every seven days. The esylate salt showed no change in purity throughout the study.

Figure 2:
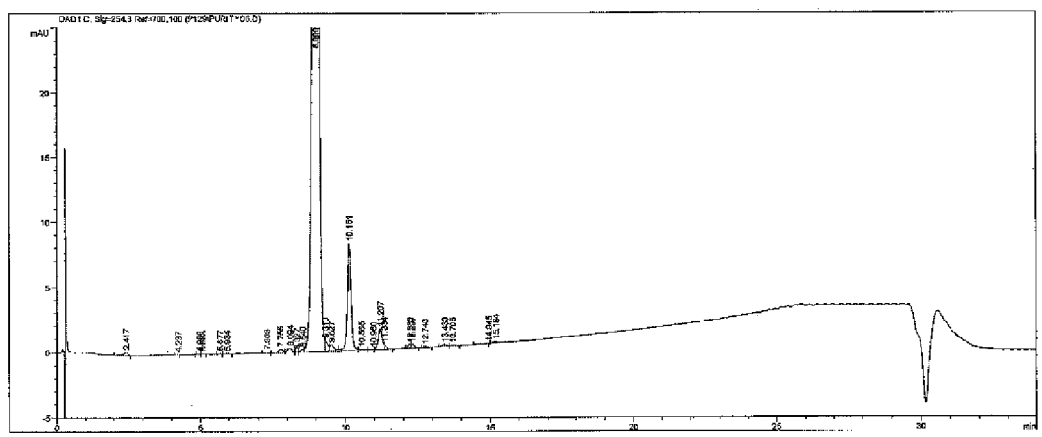
FIG. 2 shows chromatographs of LJC-039-034-1 (esylate salt) at $T^0$ and $T^4$ (and relate to the results in Table 10)
Figure 2:
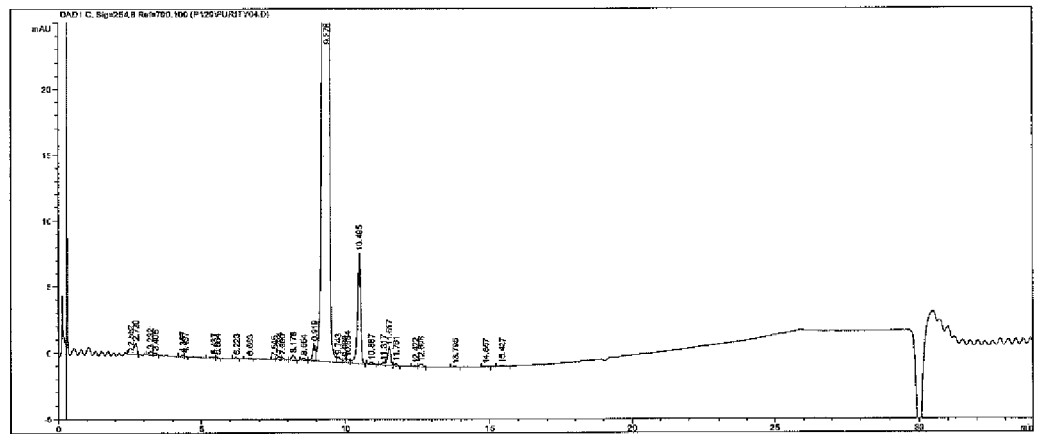

The chromatographs for the esylate salt form are shown in FIG. 2 for time points week zero and week four.

It can be seen from the chromatographs shown in FIG. 2 that there is very little change in the impurity profile of the esylate salt. A small shoulder has developed on the parent peak.

It can be seen from the powder patterns of the salts pre and post humidity studies that there are no changes in form.

Figure 3:
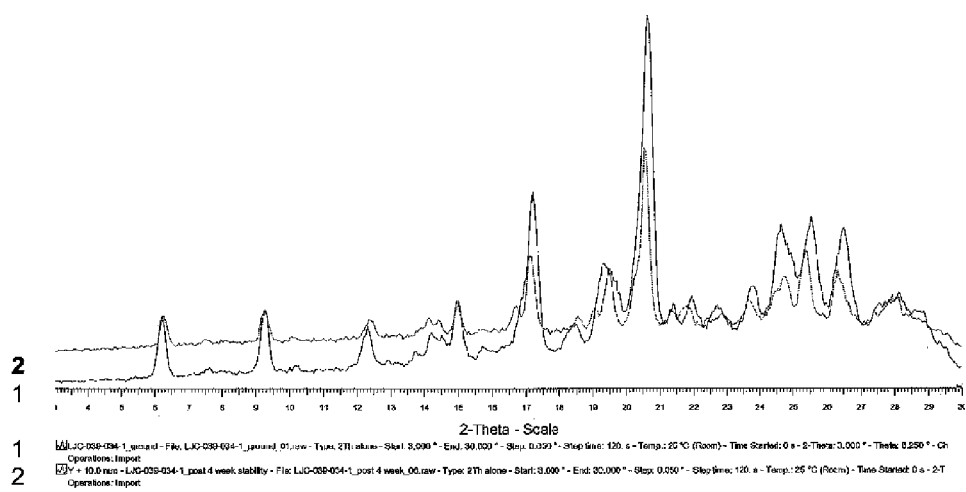
FIG. 3 shows XRPD comparing LJC-039-034-1 (esylate salt) pre and post 4 week stability study.

FIG. 3 shows XRPD comparing LJC-039-034-1 (esylate salt) pre (trace 1) and post 4 week (trace 2) stability study.

Example 5

Polymorphism Investigation

In order to determine the propensity of esylate salts to exhibit polymorphism, a maturation experiment was set up using thirty solvents (fifteen neat plus their 2.5% aqueous counterparts). The solid was slurried in various solvents (see Table 11) for one week on a heat/cool cycle from ambient to 60° C. After one week the slurries were evaporated and the solids analysed by XRPD and HPLC.

TABLE 11

Results of polymorphism investigation for esylate
Starting purity 98.6%

| entry | solvent | XRPD post 1 week | HPLC purity/ % area |
|---|---|---|---|
| 1 | acetone | Form 1 | 98.7 |
| 2 | THF | Form 1 | 98.5 |
| 3 | IPA | Form 1 | 92.5 |
| 4 | MtBE | Form 1 | 98.6 |
| 5 | DCM | Form 2 | 98.9 |
| 6 | EtOH | oiled | not analysed |
| 7 | MEK | Form 1 | 98 |
| 8 | 1,4-Dioxane | Form 1 | 98.5 |
| 9 | iPrOAc | Form 1 | 98.4 |
| 10 | DMF | solution after 7 days | not analysed |
| 11 | MeCN | Form 1 | 96.1 |
| 12 | nBuOH | solution after 7 days | not analysed |
| 13 | nPrOH | oiled | not analysed |
| 14 | MIBK | Form 1 | 97.4 |
| 15 | MeOH | amorphous | 81.2 |
| 16 | 2.5% aq acetone | Form 1 | 95.7 |
| 17 | 2.5% aq THF | amorphous | 95.1 |
| 18 | 2.5% aq IPA | oiled | not analysed |
| 19 | 2.5% aq MtBE | amorphous | 98.6 |
| 20 | 2.5% aq DCM | Form 2 | 97.9 |
| 21 | 2.5% aq EtOH | oiled | not analysed |
| 22 | 2.5% aq MEK | Form 1 | 86.5 |
| 23 | 2.5% aq 1,4-Dioxane | amorphous | 90.5 |
| 24 | 2.5% aq iPrOAc | Form 1 | 97.9 |
| 25 | 2.5% aq DMF | solution after 7 days | not analysed |
| 26 | 2.5% aq MeCN | Form 1 | not analysed |
| 27 | 2.5% aq nBuOH | solution after 7 days | not analysed |
| 28 | 2.5% aq nPrOH | oiled | not analysed |
| 29 | 2.5% aq MIBK | Form 1 | 96.4 |
| 30 | 2.5% aq MeOH | oiled | not analysed |

The maturation study of esylate showed a new form (Form 2) from DCM and aqueous DCM. The purity results post maturation show that only those slurried in methanol, aqueous MEK and aqueous dioxane degraded, suggesting the solution stability at high temperature for the esylate is good.
Investigation into New Form of Esylate In order to gain further information of the new form identified, a larger sample of LJC-039-058-1 was slurried in DCM and 2.5% aqueous DCM at 60° C. Both samples dissolved and were evaporated to dryness at ambient for analysis. The powder patterns were the same for both samples and agreed with that observed in the maturation study.

Figure 4:
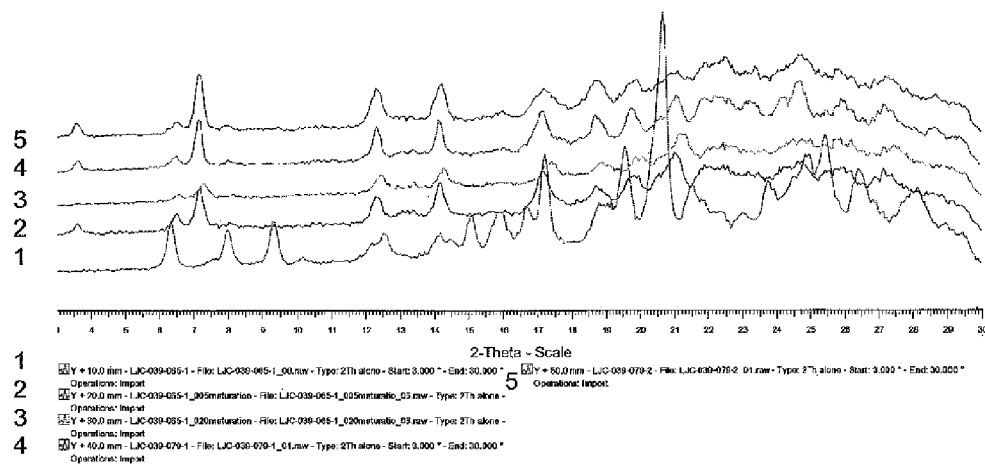
FIG. 4 shows an XRPD overlay of a new form of esylate.

FIG. 4 shows an XRPD overlay of the new form of esylate. Trace 1 shows the esylate salt (LJC-039-065-1) used as the input material for the maturation study. Traces 2 and 3 show the maturation results from DCM and aq DCM respectively. Traces 4 and 5 show the repeat maturation study from DCM and aq DCM using a different batch of esylate (LJC-039-058-1).

It is interesting to note that the esylate had been isolated previously from DCM and had shown the same form as those esylate salts isolated from other solvents, i.e. Form 1. It was only when slurrying form 1 in DCM at higher temperature that form 2 became evident.

Figure 5:
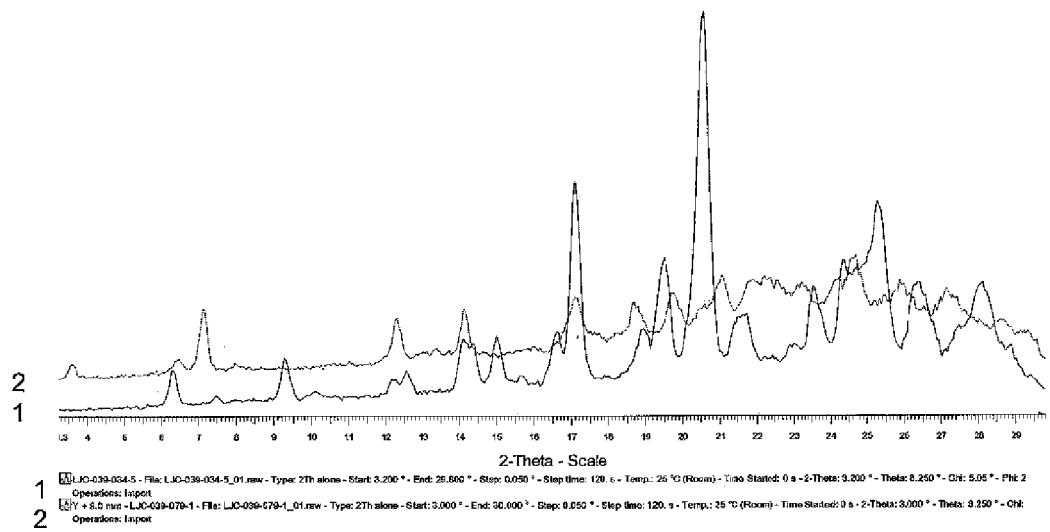
FIG. 5 shows an XRPD overlay of esylate generated in DCM and esylate slurried in DCM.

FIG. 5 shows an XRPD overlay of esylate generated in DCM and esylate slurried in DCM. Trace 1 represents the Form 1 esylate isolated from DCM (LJC-039-034-5) and trace 2 represents the outcome of the Form 1 esylate post slurry in DCM (LJC-039-079-1).

The salt screen investigations have shown that compound of formula (I) forms many salts within the appropriate pKa range, and that they are easily isolated from a range of solvents. From full characterisation of the salts, it has been determined that the esylate salts have good stability with respect to humidity. It has been concluded that there are two polymorphic forms of esylate.

Figure 6:
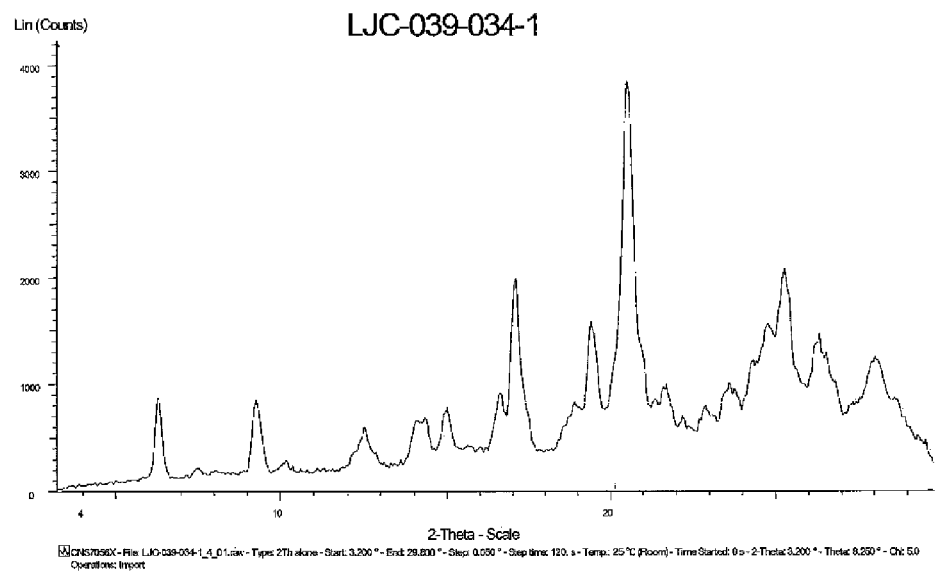
FIG. 6 shows results for esylate Form 1: A) XRPD for 100 mg batch LJC-039-034-1; B) DSC for 100 mg batch LJC-039-034-1; C) TGA for 100 mg batch LJC-039-034-1; D) $^1$H NMR for 100 mg scale batch LJC-039-034-1; E) GVS for 100 mg batch LJC-039-034-1; F) XRPD post GVS for 100 mg batch LJC-039-034-1; G) XRPD post stability study at 40° C./75% RH for LJC-039-034-1; H) VT XRPD for 100 mg batch LJC-039-034-1; I) light polarised microscopy for 100 mg batch LJC-039-034-1.
Figure 6:
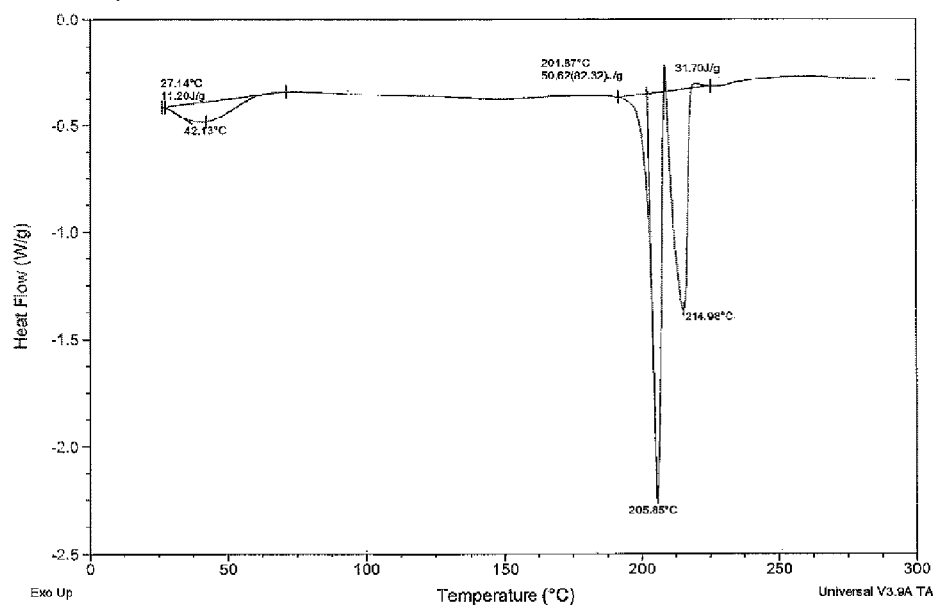
Figure 6:
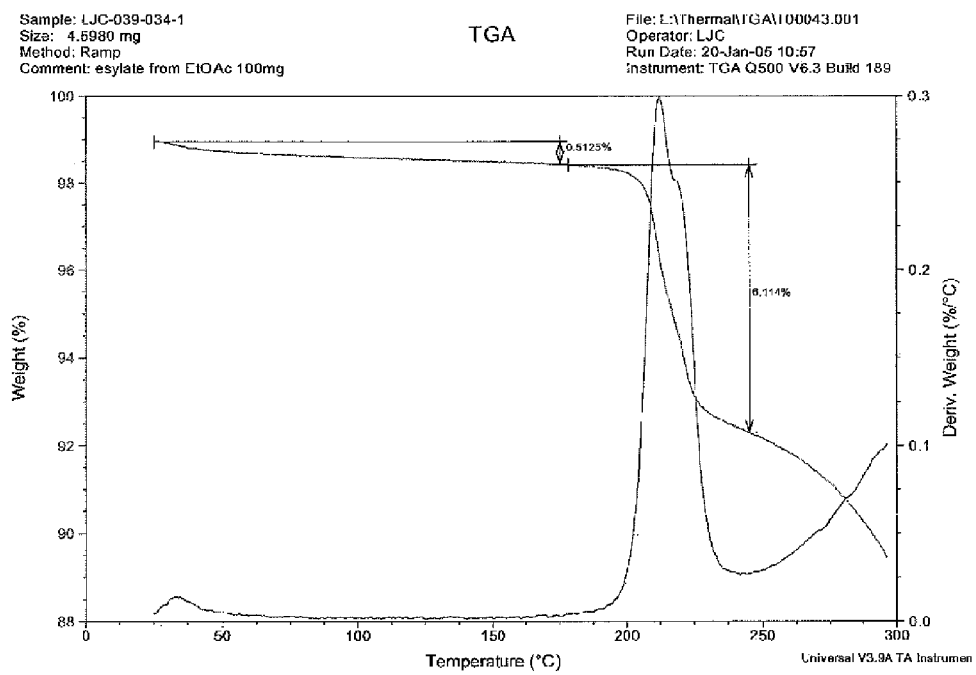
Figure 6:
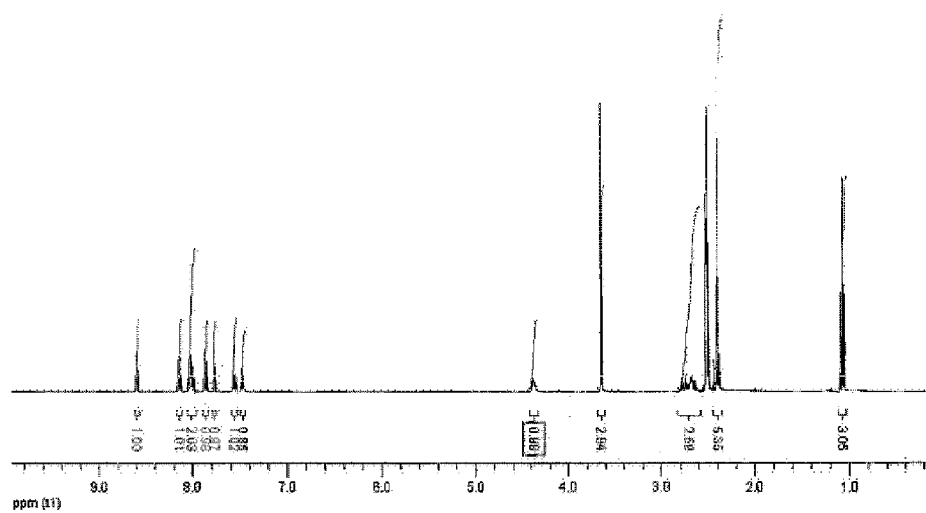
Figure 6:
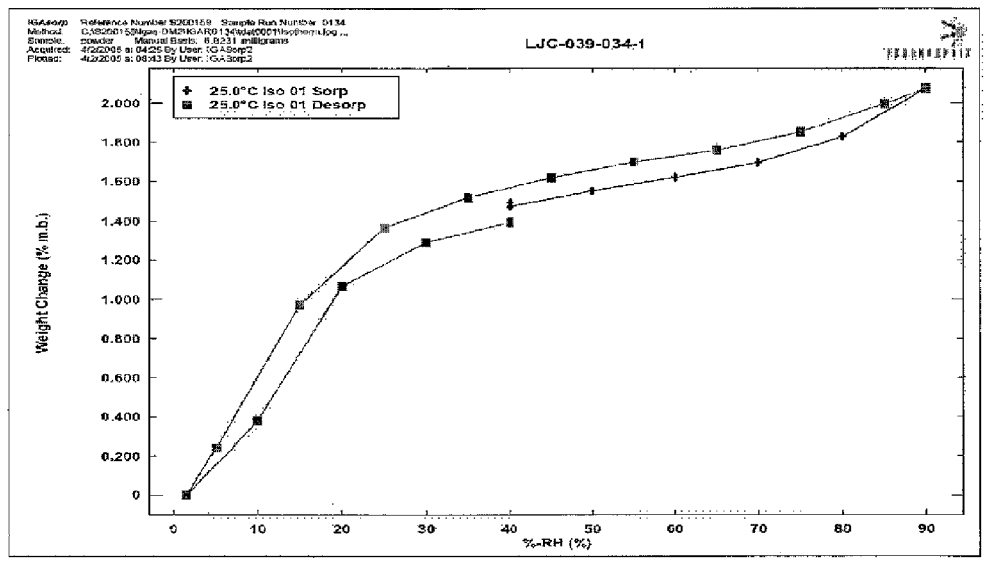
Figure 6:
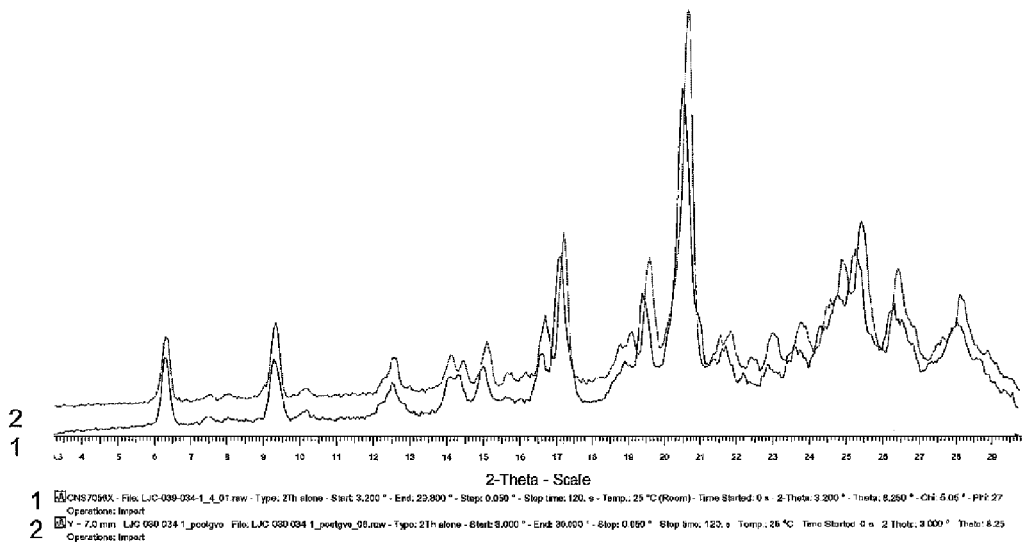
Figure 6:
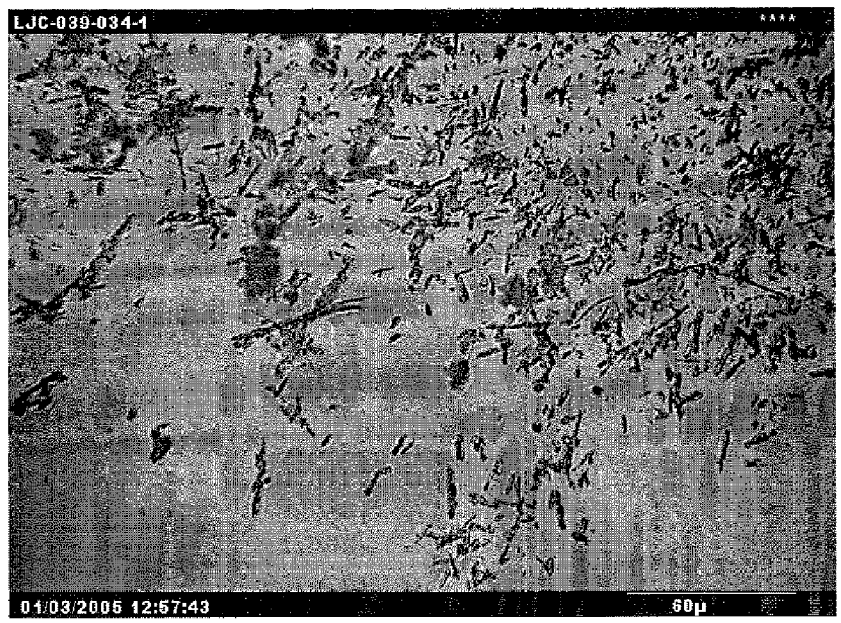
Figure 7:
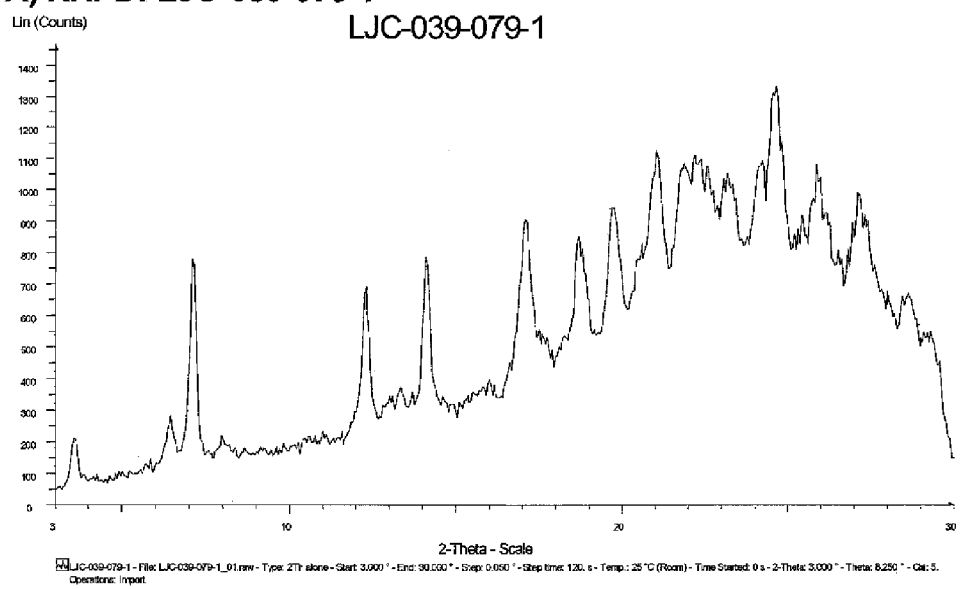
FIG. 7 shows results for esylate Form 2: A) XRPD for LJC-039-079-1; B) DSC for LJC-039-079-1.
Figure 7:
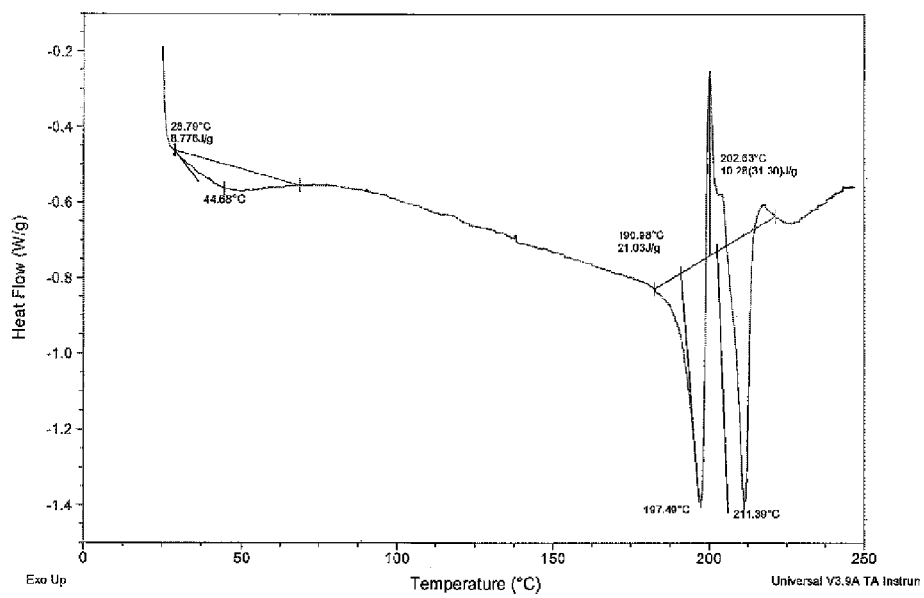

Full analytical data is shown in FIGS. 6-7 below.

Experimental Methods for Examples 2-5

Example 2

Compound of formula (I) (5 mg/well) was dissolved in solvent[1] (30 µl) in HPLC vials. To the solutions, ethane sulphonic acid (11.4 µl, 1M in ethanol) was added and the reaction mixtures stood overnight at ambient. Those vials that contained solid were dried at 40° C. under vacuum, and those that remained as solutions were concentrated by evaporation and then treated with heptane. Those that precipitated were dried as mentioned, and those that oiled were stored at 4° C.

[1] Ethanol, toluene and acetonitrile

Esylate Form 1 Scale Up

Compound of formula (I) (100 mg) dissolved in ethyl acetate (600 µl) and ethane sulphonic acid (250 µl, 1M in ethanol) added. Precipitation occurred after approximately five minutes and the reaction mixture was stirred for 80 minutes at ambient. The solid was filtered, washed with ethyl acetate and oven dried at 40° C. under vacuum for 16 hours.
Analysis Methods
Differential Scanning Calorimetry (DSC)

DSC data was collected on a TA instrument Q1000 equipped with a 50 position autosampler. The energy and temperature calibration standard was indium. Samples were heated at a rate of 10° C./min between 25 and 350° C. A nitrogen purge at 30 ml/min was maintained over the sample.

Between 0.5 and 3 mg of sample was used, unless otherwise stated, and all samples ran in a pin holed aluminium pan.
Thermogravimetric Analysis (TGA)

TGA data was collected on a TA Instrument Q500 TGA, calibrated with Alumel and running at scan rates of 10° C./minute. A nitrogen purge at 60 ml/min was maintained over the sample.

Typically 5-10 mg of sample was loaded onto a pre-tared platinum crucible unless otherwise stated.

NMR

All spectra were collected on a Bruker 400 MHz equipped with autosampler. Samples were prepared in $d_6$-DMSO, unless otherwise stated.

XRPD (X-Ray Powder Diffraction)
Bruker AXS C2 GADDS Diffractometer

X-ray powder diffraction patterns for the samples were acquired on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2-29.8°. A typical exposure time of a sample would be 120 s.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then heated to the appropriate temperature at ca. 20° C./minute and subsequently held isothermally for ca 1 minute before data collection was initiated.

Purity Analysis:
Chemical Method

Purity analysis was performed on a HP1100 Agilent:
Method: Gradient, Reverse Phase
Method Duration/min: 34
Column: Phenomenex Gemini C18 5 μm (2.0×50 mm) (Guard cartridge Phenomenex Gemini C18 guard cartridge 2×4 mm)
Column Temperature/° C.: 40
Injection/μl: 5
Flow Rate ml/min: 0.8
Detection: UV
Wavelength/nm: 255 (bandwidth of 90 nm), 240 (bandwidth of 80 nm), 254 (bandwidth of 8 nm)
Phase A: 2 mmol $NH_4HCO_3$ (adjusted to pH 10 with $NH_3$ solution)
Phase B: Acetonitrile
Timetable:

| Time/Min | % A | % B |
|---|---|---|
| 0 | 90 | 10 |
| 25 | 10 | 90 |
| 28.8 | 10 | 90 |
| 29 | 90 | 10 |
| 34 | 90 | 10 |

Chiral Method
Purity analysis was performed on a Gilson HPLC system:
Method: Isocratic, Normal Phase
Method Duration/min: 50
Column: Diacel Chrialcel OJ-H (5 μm) 4.6×250 mm (Guard cartridge Diacel Chrialcel OJ-H analytical guard cartridge 5 μm 4.0×10 mm)
Column Temperature/° C.: 40
Injection/μl: 10
Flow Rate ml/min: 1.0
Detection: UV
Wavelength 1 nm: 225 (single wavelength detector)
Phase A: hexane
Phase B: ethanol
Timetable:

| Time/Min | % A | % B |
|---|---|---|
| 0 | 93 | 7 |

Gravimetric Vapour Sorption (GVS) Studies

All samples were run on a Hiden IGASorp moisture sorption analyser running CFRSorp software. Sample sizes were typically 10 mg. A moisture adsorption desorption isotherm was performed as outlined below (2 scans giving 1 complete cycle). All samples were loaded/unloaded at typical room humidity and temperature (40% RH, 25° C.). All samples were analysed by XRPD post GVS analysis. The standard isotherm was performed at 25° C. at 10% RH intervals over a 0-90% RH range unless otherwise stated.

| Scan1 | Scan2 | |
|---|---|---|
| Adsorption | Desorption | Adsorption |
| 40 | 85 | 10 |
| 50 | 75 | 20 |
| 60 | 65 | 30 |
| 70 | 45 | 40 |
| 80 | 35 | |
| 90 | 25 | |
| | 15 | |
| | 5 | |
| | 0 | |

Solubility

This was measured by suspending enough compound in 0.25 ml of solvent (water) to give a maximum final concentration of 10 mg/ml of the parent free form of the compound. The suspension was equilibrated at 25° C. for 24 hrs followed by a pH check and filtration through a glass fibre C 96 well plate. The filtrate is then diluted down 101×. Quantitation was by HPLC with reference to a standard dissolved in DMSO at approx 0.1 mg/ml. Different volumes of the standard, diluted and undiluted tests were injected. The solubility was calculated by integration of the peak area found at the same retention time as the peak maximum in the standard injection. If there is sufficient solid in the filter plate the XRPD is normally checked for phase changes, hydrate formation, amorphization, crystallization etc.

TABLE

| Time/min | % Phase A | % Phase B |
|---|---|---|
| 0.0 | 95 | 5 |
| 1.0 | 80 | 20 |
| 2.3 | 5 | 95 |
| 3.3 | 5 | 95 |
| 3.5 | 95 | 5 |
| 4.4 | 95 | 5 | pKa Determination pka determination was performed on a Sirius GlpKa instrument with D-PAS attachment. Measurements were made by potentiometric titration in MeOH:H2O mixtures at 25° C. The titration media was ionic strength adjusted with 0.15M KCl. The values found in the MeOH:$H_2O$ mixtures were extrapolated to 0% co-solvent via a Yasuda-Shedlovsky extrapolation.

Potentiometric titration performed on a Sirius GlpKa instrument using three ratios of Octonol:ISA water generated Log P, Log $P_{ion}$, and Log D values.

Hot Stage Microscopy

Hot stage microscopy was studied using a Leica LM/DM polarised microscope combined with a Mettler-Toledo MTFP82HT hot-stage in the temperature range 25-350° C. with typical heating rates in the range 10-20° C./min. A small amount of sample was dispersed onto a glass slide with individual particles separated as well as possible. Samples were viewed under normal or cross-polarised light (coupled to a λ false-colour filter) with a ×20 objective lens.

Chiral Purity Method

| System setup | |
|---|---|
| Pump: | Gilson 322 binary pump |
| Detector: | Gilson 152 UV/Vis |
| Autosampler: | Gilson 233XL rack + Gilson 402 dual syringe pump |
| Column oven: | Phenomenex Thermasphere TS-130 |
| Software: | Gilson Unipoint LC software |
| Column: | Daicel Chiralcel OJ-H, 5 µm, 4.6 × 250 mm |
| Guard column: | Daicel Chiralcel OJ-H analytical guard cartridge, 5 µm, 4.6 × 10 mm |
| HPLC conditions | |
| Channel A: | Hexane (93%) |
| Channel B: | Ethanol (7%) |
| Flow rate: | 1.0 ml/min |
| Detector wavelength | 225 nm |
| Column Temperature: | 40° C. |
| Run time: | 50.0 mins |

Sample Conditions

Approximately 0.2 mg of sample was dissolved in the appropriate volume of Hexane:Ethanol 1:1 v/v to give a 0.2 mg/ml solution. This was capped and placed on a vortex mixer at high speed for a duration of ~15 seconds. If solid remained at this point, then the sample vial was sonicated for approximately 10 seconds followed by a further 10 to 15 seconds on the vortex mixer. 10 µl was injected onto the HPLC system. Samples were injected in duplicate following an initial duplicate injection of Hexane:Ethanol 1:1 v/v as a blank.

What is claimed is:

1. An esylate salt of a compound of formula (I):

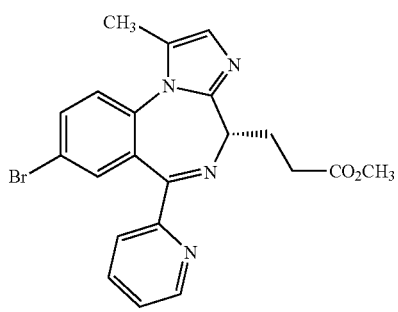

(I)

which is a crystalline salt.

2. The esylate salt according to claim 1 which is a crystalline polymorph that exhibits an X-ray powder diffraction pattern which comprises characteristic peaks at 6.2, 9.2, 12.3, 15.0, 17.2, and 20.6 degrees two-theta.

3. The esylate salt according to claim 1 which is a crystalline polymorph that exhibits an X-ray powder diffraction pattern which comprises characteristic peaks at 3.6, 6.4, 7.1, 12.3, 14.1, and 17.1 degrees two-theta.

4. A pharmaceutical composition comprising a salt according to claim 1, and a pharmaceutically acceptable carrier, excipient, or diluent.

5. A method of making a salt according claim 1, which comprises reacting a free base of a compound of formula (I) with ethane sulphonic acid.

6. The method according claim 5, which comprises contacting the free base of a compound of formula (I) with ethane sulphonic acid in solution to cause formation of a precipitate of the esylate salt.

7. The method according to claim 6, which further comprises isolating the precipitate.

8. The method according to claim 6, wherein the free base is dissolved in toluene or ethyl acetate.

9. The method according to, claim 6, wherein the ethane sulphonic acid is dissolved in ethanol.

10. The method according to claim 5 of preparing wherein the salt is a crystalline polymorph that exhibits an X-ray powder diffraction pattern which comprises characteristic peaks at 6.2, 9.2, 12.3, 15.0, 17.2, and 20.6 degrees two-theta, wherein the free base of the compound of formula (I) is in a solution selected from the group consisting of toluene, ethanol, ethyl acetate, MtBE, DCM, acetone, isopropyl acetate, ethyl formate, and methanol and contacting the solution with a solution of ethane sulphonic acid in ethanol to cause formation of a precipitate of the salt.

11. The method according to claim 6 of preparing a salt, which comprises slurrying the esylate salt of a compound of formula (I) which is a crystalline polymorph that exhibits an X-ray powder diffraction pattern which comprises characteristic peaks at 3.6, 6.4, 7.1, 12.3, 14.1, and 17.1 degrees two-theta, with DCM, or aqueous DCM at a temperature above room temperature to form a solution, and evaporating the solution to dryness.

12. A method of preparing a salt according to claim 1, which comprises crystallizing a compound of formula (I) esylate from a solvent, or from a solvent/anti-solvent or solvent/co-solvent mixture.

13. A method for producing sedation or hypnosis in a subject, which comprises administering an effective sedative or hypnotic amount of a salt according to claim 1 to the subject.

14. A method for inducing anxiolysis in a subject, which comprises administering an effective anxiolytic amount of a salt according to claim 1 to the subject.

15. A method for inducing muscle relaxation in a subject, which comprises administering an effective muscle relaxant amount of a salt according to claim 1 to the subject.

16. A method for treating convulsions in a subject, which comprises administering an effective anticonvulsant amount of a salt according to claim 1 to the subject.

17. A method of producing a medicament comprising an esylate salt of a compound of formula (I):

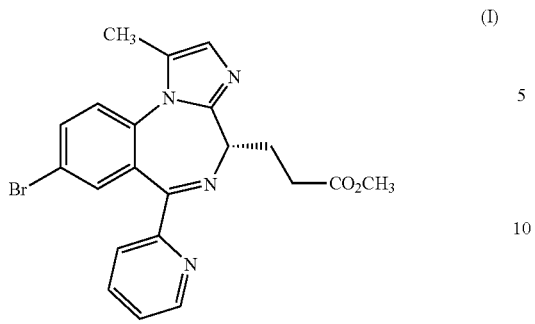

and combining it with a suitable carrier.

18. The method of claim 17, wherein the medicament comprises an amount of the salt sufficient to induce a sedation or hypnosis in a subject.

19. The method of claim 17, wherein the medicament comprises an amount of the salt sufficient to induce anxiolysis in a subject.

20. The method of claim 17, wherein the medicament comprises and amount of the salt sufficient to induce muscle relaxation in a subject.

21. The method of claim 17, wherein the medicament comprises an amount of salt sufficient have an anticonvulsant effect in a subject.

* * * * *

UNITED STATES PATENT AND TRADEMARK OFFICE
CERTIFICATE OF CORRECTION

PATENT NO. : 8,642,588 B2  
APPLICATION NO. : 12/373457  
DATED : February 4, 2014  
INVENTOR(S) : Gary Stuart Tilbrook et al.

Page 1 of 1

It is certified that error appears in the above-identified patent and that said Letters Patent is hereby corrected as shown below:

In the Claims

Column 16, line 26 (claim 10, first line): delete "of preparing".

Column 17, line 24 (claim 20, second line): replace "and amount" with --an amount--.

Column 17, line 27 (claim 21, second line): replace "sufficient have" with --sufficient to have--.

Signed and Sealed this  
Third Day of June, 2014

Michelle K. Lee  
*Deputy Director of the United States Patent and Trademark Office*